United States Patent [19]

Megeed

[11] Patent Number: 5,147,441

[45] Date of Patent: Sep. 15, 1992

[54] BIOLOGICAL PRODUCT FOR SOIL IMPROVEMENT AND METHOD OF APPLICATION TO SOIL

[76] Inventor: Mohamed E. A. Megeed, Montana State Univ., Plant Path Dept., Bozeman, Mont. 59717

[21] Appl. No.: 708,383

[22] Filed: May 31, 1991

[51] Int. Cl.$^5$ .............................................. C05G 3/08
[52] U.S. Cl. .............................................. 71/7; 71/6; 71/902; 435/252.4
[58] Field of Search ............................. 71/6, 7, 902; 435/252.4

[56] References Cited

FOREIGN PATENT DOCUMENTS 0051684  3/1985  Japan ........................................ 71/7
8401686  5/1984  PCT Int'l Appl. ......................... 71/7

Primary Examiner—Ferris Lander
Attorney, Agent, or Firm—Kerkam, Stowell, Kondracki & Clarke

[57] ABSTRACT

A biological product for actively producing nitrogen and phosphate enrichment of soil comprising a nitrogen-fixing effective amount of *Azospirillum sp.* M32, an amount of *Bacillus polymixa* M7 sufficient to produce polymyxin, an anti-microbial peptide active against Gram negative bacteria which converts phosphorous materials fixed in the soil to which it is applied to a phosphate in plant-available forms, and a nutrient for the bacteria comprising a cellulosic material containing cellulose as an integral component selected from the group consisting of straw, xylan, hemicellulose and lignin, as well as other organic carbon or nitrogen materials.

6 Claims, No Drawings

BIOLOGICAL PRODUCT FOR SOIL IMPROVEMENT AND METHOD OF APPLICATION TO SOIL

BACKGROUND OF THE INVENTION

1. Field of the Invention

The present invention relates to biological soil improvement products and methods for their application to soil.

2. Description of the Prior Art

Certain Azospirillum and Bacillus bacteria are known to be useful as nitrogen-fixing organisms for plants in soil [Japanese Patent No. 60-051684 and Russian Patent No. 1,210,383.]. It is also known that *Bacillus polymixa* possesses anti-bacterial activity, particularly against Gram negative bacteria.

Microorganisms have been employed in soil treatments as far back as the last century. See, e.g., "Bacteria In Relation to Country Life," J. Lipman, MacMillan Co., New York (1912); and "The Micro-Organisms of the Soil," Sir E. John Russell, Longmano, Green & Co., London (1923). However, this use consisted for the most part of the one or two specific microorganisms or a "grab bag" mixture of soil cultures that were not specifically identified or quantified. Some were nothing more than composted manures carrying groups of microorganisms typically found in such waste. The beneficial activity of such unquantified mixtures on the soil resulted in increased crop yields. More recently, there have been more sophisticated microbial formulations and specific characteristics of individual formulations documented. See, e.g., "Biological Control of Plant Pathogens," K. Baker et al., W. H. Freeman & Co., San Francisco (1974); "Beneficial Bacteria Enhance Plant Growth," T. Suslow et al., U. California Dir. Agri. St. Reports, *California Agriculture*, Vol. 33, No. 11-12, pp. 15-17 (Nov./Dec. 1979); and "*Microbial Interactions in Soils and Health Plant Growth*," A. M. Smith, *Australian Plant*, Vol 9, No. 73, pp. 209-212 (Dec. 1977).

However, actual use of specific groups of organisms on plants met with varying degrees of success depending on other non-controlled variables. Such variables include: (1) the presence of absence of adequate micro- and macro-nutrients in the soil to support the propagation of the microorganisms; (2) the amount of organic material able to hold nutrients and microbes to create a suitable environment for microbial growth; and (3) the presence or absence of certain minerals required by the plant for proper uptake of the nutrients provided by the microbial activity.

It is an object of the invention to provide an improved biological product for improving the plant growth capability of soil which synergistically combines the activities of specific Azospirillum and Bacillus bacteria.

SUMMARY OF THE INVENTION

The foregoing and other objects are realized by the present invention which provides an improved biological product for actively producing nitrogen and phosphate enrichment of soil comprising a nitrogen-fixing effective amount of Azospirillum sp., an amount of *Bacillus polymixa* sufficient to produce polymyxin, an anti-microbial peptide active against Gram negative bacteria which disrupts the structure of the outer membranes and converts phosphorous compounds in the soil to which it is applied to a phosphate in plant-available forms, and a nutrient or the bacteria comprising a cellulosic material containing cellulose as an integral component selected from the group consisting of straw, xylan, hemicellulose or lignin, as well as other organic components of the organic mix.

DETAILED DESCRIPTION OF THE INVENTION

Straw residues constitute a large reservoir of difficult-to-degrade carbon compounds with the potential to provide sufficient energy for agriculturally significant levels of nitrogen fixation and phosphate solubilizing activities. Straw is a complex mixture of cellulose, hemicellulose, pectins and lignins with 40% of their dry weight constituting carbon. This large reservoir or energy is available for utilization for heterotrophic growth and nitrogen fixation, as well as biological phosphate solubilizing activities.

Azospirillum Sp. M32, a heterotrophic nitrogen fixer, has been isolated from soil and root samples from different locations around the world. It has been proved to be associated with the grasses, cereals and legumes. Azospirillum sp. M32 can utilize a wide variety of complex materials as an energy and carbon source. It has the ability to utilize xylan and straw (hemicellulose) as an energy and carbon source for nitrogen fixation and growth. Mixtures of Azospirillum sp. M32 and Bacillus sp. M7 are also capable of fixing nitrogen utilizing the degradation products of the hemicellulose and other organic compounds.

Azospirillum sp. M32 can be used to promote straw breakdown and thus enhance the nitrogen status of the organic material and the soil.

Mixing *Bacillus polymixa* M7 with Azospirillum sp. M32 synergistically improves the nitrogen fixation activity of the latter.

The nitrogen input to the soil produced by the mixture of microorganisms range between 1.2-1.46% of the amount of cellulosic material decomposed.

Low-grade rock phosphate deposits (less than 25% $P_2O_3$) are unsuitable for processing into superphosphate. Also, in neutral to alkaline soil, the direct application of rock phosphate and even the superphosphate will not be of much utility.

Mixing the organic materials with phosphate-solubilizing microorganisms and low-grade phosphate has proven to be very effective in promoting phosphate solubilization.

Premixing and incubating the compost mixture of rock phosphate, organic fertilizer and phosphate-solubilizing microorganisms help to upgrade the organic fertilizer value to become more balanced in the fertilizer elements (N, P, K); give the microorganisms the chance to express their effects (using the organic components as a carbon and energy source) to produce enough acidity to solubilize the rock phosphate and change its form to the mono- and di- form which is more utilizable by the plants; increase the population of the microorganisms in the organic fertilizers which will be considered as a soil inocula; and eliminate or delay direct contact between the seed (seed coating techniques normally used) and the acid-producing bacteria to the stage that the seedling can withstand the acidity. Moreover, the bacteria will not compete with the other microorganisms on the plant excretion on the root surface which could be left to other useful activities and biotransformation processes.

Bacillus bacteria are known to produce anti-bacterial materials (polymyxin) which help in controlling the Gram negative bacteria (disrupt the structure of the outer membranes) in the organic fertilizers.

The two microbial components of the present invention were tested for mutual antagonism using the disc method. No antagonistic activities were detected between them.

The microbial mixture (nitrogen fixers with the ability to utilize cellulosic materials as well as other organic materials and phosphate solubilizing bacteria) greatly upgrades the organic fertilizer value to become more balanced in the fertilizer elements which help in degrading the cellulosic materials, assimilating the nitrogen content and increasing the availability of the phosphate element to the plant uptake.

Both microorganisms can grow on LB broth which contains tryptone (10 g/l), yeast extract (5 g/l) and NaCl (10 g/l) under the following growth conditions: temperature of 30° C., shaking at 500 rev/min at a pH of 7.0 for a period of 2-3 days. The mixture can be sprayed on the cellulosic containing material in a saline solution such that the material contains $10^6$ cells per gram.

The performance of any organic fertilizer primarily depends on the type and the level of the microbial activities in the given soil. The term "performance," as used herein, refers to the linkage between the fertilizer elements supplied in the organic mix and the plant fertilizer requirements which basically is an indirect linkage and should first go through the microbial transformation colum (soil).

Under some soil conditions, the microbial transformation colum negatively affects the availability of the fertilizer elements in the organic mix. Thus, it is an obligation of the organic mix producers to specify the optimum soil conditions to obtain the highest performance of their products or modify their formulae to adapt to all soil conditions prevailing in any given ecosystem to give 100% of the plant requirements form the N, P, K elements.

Azospirillum sp. M32 is a soil native nonpathogenic heterotrophic bacteria; thus, it has the capability to transform the atmospheric nitrogen into organic nitrogen ($NH_4$) in the soil ecosystem.

Azospirillum sp. M32 is attractive to the plant rhizosphere (the part of the soil which adjusts to the root hairs) due to the reduced oxygen and the plant excretions. Organic matter stimulates the Azospirillum sp. M32 and enhances its nitrogen fixation potential.

The addition of organic fertilizer mix to the soil with high C/N ratio (without the nitrogen-fixing and phosphate-releasing bacteria) could enhance all heterotrophic activities which degrade the carbon and the nitrogen materials in the organic mix as a source of carbon and energy an immobilize all available nitrogen into microbial protein. The high efficiency of the bacterial transformation would compete with the standing plant and reduce plant growth.

Azospirillum sp. M32 has the ability to utilize the organic mix degradation products to fix, excrete and enrich the soil environment around the plant roots with the nitrogenous material.

Bacillus polymixa M7 as a phosphate-releasing heterotrophic bacteria with its proteinanse activities will also help in the degradation of the organic nitrogen component in the organic mix and provide an available nitrogen material to the plant. During the protein degradation, Bacillus polymixa M7 as a heterotrophic bacteria produces organic acids which change the soil reaction in the soil microenvironment leading to the solubilization and release of the phosphate into plant-available forms. Bacillus polymixa M7 also produces polymyxin, an anti-microbial peptide active against Gram negative bacteria.

The incorporation of phosphate-releasing and nitrogen-fixing bacteria in the organic mix provides a self-positive transformation potential to enhance its performance under diverse soil conditions.

Soil organic matter is the greatest single component factor controlling the production of both cultivated and non-cultivated soils. On the other hand, the soil organic matter fraction is frequently a severely abused aspect of any ecosystem management plan. Thus, any increase in organic matter input has a positive impact on the total amount of soil organic matter.

Soil organic matter plays a major role in soil structure (enhances the soil aggregation), soil water penetration, root development and enhances the soil microbial activities (nitrogen fixation, etc.), as well as the erosion resistance of the soil. It is a source of the major nutrients (N, S, P, etc.). The humidified materials give color to the soil, provide cation absorption capacity and assist in the slow release of nutrients, buffering action and inactivation of the organic pesticides.

Soil organic matter is a collection of decomposing residues, by-products formed by organisms, soil microorganisms and non-decomposable materials. Humin, fulvic and humic acids are the main components of the steady-state soil organic matter (humates). Fulvic acid has an open structure, is flexible, is perforated by voids of varying dimensions and can trap organic and inorganic compounds. Humic acid is formed by polycondensation of similar, but not identical, constituents so no two humic molecules will be identical. The humates are adsorbed to clay minerals by polyvalent cations such as $Ca^{+2}$ and $Fe^{+2}$ or by association with hydrous oxides.

Soil microorganisms are heavily involved in humic and fulvic acid synthesis through modification of the organic components of the organic fertilizer to humic substance precursors, as well as direct synthesis of the humic acid-like polymers which could be incorporated directly into the humic acid complex comprising the mature humic pool.

The addition of organic fertilizer mix with more decomposable materials to the cultivated soil activates the mineralization potential of the soil biota, i.e., the transformation of organic forms of a mineral into inorganic forms of the mineral to provide energy and carbon for microbial growth and reproduction. On the other hand, the phosphate dissolving microorganisms have the ability to mineralize (dissolve) the phosphorous from the complex compounds (inorganic or organic) to release the phosphate into available forms through the action of extracellular enzymes (keratinolytic, proteolytic and organic acids which change the soil reaction in the soil microenvironment).

To maximize the beneficial effects of the organic matter additions, it must be stressed that the more humified residues present in the organic fertilizer mix, the greater the organic matter accumulation in the form of humic, fulvic and humin acids. Organic fertilizer mix with these formulae should not encourage the mineralization or the immobilization of the available nutrients. With more decomposition activities, the microbial community would be active, but the processes would be sufficiently slow to encourage greater humification.

TABLE 1

NITROGEN CONTENT (%) OF SORGHUM PLANT (SORGO HAY) GROWN IN SOIL TREATED WITH ORGANIC FERTILIZER

| Treatment | 60 Days | 90 Days |
|---|---|---|
| Azospirillum sp. M32 + 2% Organic fertilizer | 1.46$^a$ | 1.78$^a$ |
| 2% Organic fertilizer | 1.228$^b$ | 1.404$^b$ |
| Control | 1.08$^c$ | 1.344$^b$ |

LSD (0.05) = 0.104

TABLE 2

EFFECT OF DUAL INOCULATION OF SORGHUM PLANT ON PHOSPHATE-RELEASING ACTIVITY*

| Treatment | 2 wks | 4 wks | 6 wks | 8 wks |
|---|---|---|---|---|
| Bacillus polymixa M7 | 28 | 19 | 25 | 17.4 |
| Azospirillum sp. M32 | 3.4 | 6.5 | 6.8 | 10.3 |
| M7 + M32 | 42.2 | 31.2 | 25.2 | 18.7 |
| Control | 2.2 | 4.2 | 4.6 | 6.5 |

*Soluble phosphate (mg/100 g dry soil)

The organic fertilizer mix of the present invention is designed to contain a greater amount of highly humified organic materials with a carbon/nitrogen ratio that is well adapted to increase the soil content of humic, fulvic and humin materials. It also enhances the phosphate dissolving and nitrogen fixation activities.

The material can be applied to newly cultivated land to build up the organic components of the soil profile and to increase the beneficial effects of the fertilizer. It can also be used in previously cultivated land to restore the level of humic and fulvic acids in the soil to enhance water retention and the stability of the soil profile.

I claim:

1. An improved biological product for actively producing nitrogen and phosphate enrichment of soil comprising a nitrogen fixing effective amount of Azospirillum sp. M32, an amount of Bacillus polymixa M7 sufficient to produce polymyxin, which is an anti-microbial peptide active against Gram negative bacteria which converts phosphorus compounds in the soil to which it is applied to a phosphate in plant-available forms, and a nutrient for said bacteria utilizing a cellulosic material containing cellulose as an integral component selected from the group consisting of straw, xylan, hemicellulose and lignin.

2. The product of claim 1 additionally containing a source of phosphorous elements soluble by said Bacillus polymixa M7 to produce a phosphate in plant available forms.

3. The product of claim 1 additionally containing organic material having a carbon/nitrogen ratio adapted for conversion by microorganisms to produce humin, fulvic and humic acids and to enhance the activities of said bacteria.

4. A method for improving soil and enhancing plant growth therein comprising applying thereto an amount of the biological product of claim 1.

5. A method for improving soil and enhancing plant growth therein comprising applying thereto an effective amount of the biological product of claim 2.

6. A method for improving soil and enhancing plant growth therein comprising applying thereto an effective amount of the biological product of claim 4.

* * * * *